United States Patent [19]

Jenneman et al.

[11] Patent Number: 5,686,293
[45] Date of Patent: Nov. 11, 1997

[54] SULFIDE-OXIDIZING BACTERIA

[75] Inventors: Gary E. Jenneman, Bartlesville, Okla.; Diane Gevertz, San Diego, Calif.

[73] Assignee: Phillips Petroleum Company, Bartlesville, Okla.

[21] Appl. No.: 499,721

[22] Filed: Jul. 7, 1995

[51] Int. Cl.$^6$ ............................................. C12N 1/20
[52] U.S. Cl. ..................... 435/252.1; 435/281; 435/282; 435/262; 435/264; 435/266
[58] Field of Search ........................ 435/266, 282, 435/262, 264, 252.1, 281

[56] References Cited

U.S. PATENT DOCUMENTS

| | | | |
|---|---|---|---|
| 4,760,027 | 7/1988 | Sublette | 435/266 |
| 4,968,622 | 11/1990 | Berzaczy et al. | 435/266 |
| 5,196,129 | 3/1993 | Luisi | 252/49.5 |
| 5,236,677 | 8/1993 | Torres-Cardona et al. | 423/230 |
| 5,366,891 | 11/1994 | Premuzic et al. | 435/262 |

FOREIGN PATENT DOCUMENTS

| | | | |
|---|---|---|---|
| 0 218 958 | 9/1986 | European Pat. Off. | B01D 53/00 |
| WO 95/24960 | 9/1995 | WIPO . | |

OTHER PUBLICATIONS

Biotechnology and Bioengineering, vol. 35, pp. 1150-1154 (1990; Cadenhead et al).

Biotechnology and Bioengineering, vol. 37, pp. 4997-504 (1991; Ongcharit et al).

Applied Biochemistry and Biotechnology, vol. 34, pp. 811-817 (1992; Sublette).

Wat. Res., vol. 27, No. 5, pp. 839-846 (1993; Lee et al).

Vishniac, Genus 1. Thiobacillus, IN: Bergey's manual of determinative bacteriology, 8th edition, Buchanan and Gibbons, eds. pp. 456-460, 1974.

*Primary Examiner*—Jean C. Witz
*Attorney, Agent, or Firm*—Lucas K. Shay

[57] ABSTRACT

A bacterial culture which comprises a Campylobacter-like species is provided. The bacterial culture is capable of oxidizing a sulfide compound in a fluid such as, for example, a produced brine. Also provided is a process for substantially reducing sulfide content in a fluid wherein the process comprises contacting the fluid with a bacterial culture which comprises a Campylobacter-like species.

14 Claims, 2 Drawing Sheets

5,686,293

1

SULFIDE-OXIDIZING BACTERIA

FIELD OF THE INVENTION

This invention relates to bacteria capable of oxidizing a sulfide compound or substantially reducing sulfide content in brines, oil, gas, or combinations of any two or more thereof. This invention also relates to a process for substantially reducing sulfide content in brines, oil, gas, or combinations of any two or more thereof.

BACKGROUND OF THE INVENTION

Sulfides, especially soluble sulfides ($H_2S$, $HS^-$, $S^{2-}$, or combinations thereof), frequently detected in brines such as, for example, oil field brines as a consequence of the activities of sulfate-reducing bacteria (SRB), pose serious problems for industries due to its toxicity, odor, corrosive nature, and potential for well bore plugging. Current treatment technologies for sulfide removal include physical/chemical methods such as stripping with steam or flue gas, air oxidation, and precipitation. However, microbial treatment may be a more efficient and cost-effective alternative for reducing sulfide levels.

Petroleum reservoirs harbor distinct microbial communities that contain a variety of physiological types of bacteria. Fermentative bacteria, hydrocarbon-oxidizers, denitrifiers, methanogens and SRB have all been isolated from reservoir brines. SRB are of primary concern to the petroleum industry due to their ability to reduce sulfates to sulfides thereby contributing to the deleterious role in the plugging of injection wells, corrosion of equipment, and souring of gas, oil, or both. The cost of oil production is increased significantly because of equipment failure, additional equipment needed to remove sulfide, the need for biocides to control microbial growth, and additional chemicals needed to remove or prevent iron sulfide scale.

Sulfide production generally depends on a number of nutritional and physical factors that influence the growth of SRB in, for example, oil reservoirs. The concentrations of utilizable carbon, sulfate, nitrogen and phosphorus, also affect the growth of SRB and sulfate reduction rates.

Other bacteria may also play a role in corrosion and reservoir souring. For instance, numerous strains of *Shewenella putreficians* have been isolated from oil field brines and related fluids which can grow anaerobically by reducing sulfur oxyanions other than sulfate to hydrogen sulfide.

Traditionally, the petroleum industry has used biocides, such as, for example, quaternary ammonium compounds, isothiazolone derivatives, glutaraldehyde, formaldehyde, acrolein, or combinations of any two or more thereof to control SRB. The success of this approach is limited, however, by the propensity of bacteria to form biofilms, which are relatively impermeable to biocides.

Biological approaches for the control of SRB have been investigated as alternatives to physical/chemical treatment. The addition of high concentrations of nitrate to enrichment cultures amended with sulfate and various electron donors has been reported to result in inhibition of biogenic sulfide production for prolonged periods of time.

Nitrate has also been used as an electron acceptor for anaerobic sulfide oxidation. Nitrate-dependent sulfide oxidation by endogenous bacteria in water associated with oil, gas, or both, production has been demonstrated in laboratory studies with rock cores, as well as in field tests, where sulfide levels declined 40 to 60% in brines from three adjacent production wells 45 days after the injection of nitrate into the formation. Most of the research on bio-oxidation of sulfide in brines, gas streams, and crude petroleum has focused on the use of exogenous species of Thiobacillus. In a field demonstration to remediate sour produced water, *Thiobacillus denitrificans*, strain F, efficiently oxidized sulfide aerobically to sulfate, despite several upsets to the system.

Oxidizing sulfides to sulfates does not appear to be the solution because sulfates can be again reduced by SRB to sulfides thereby creating the problems illustrated above. Therefore, there is an ever-increasing need to develop a bacterial culture that can oxidize a sulfide or portions thereof to elemental sulfur and to develop a process for substantially oxidizing a sulfide, or substantially reducing sulfide content, in a fluid such as brines, oil, gas, or combinations of any two or more thereof. Development of such bacterial culture, or process, or both, would also greatly contribute to better understanding of applications, limitations, or combinations thereof in biotreatments of brines, oil, gas, or combinations of any two or more thereof.

SUMMARY OF THE INVENTION

An object of this invention is to provide a bacterial culture or a bacterium which is capable of substantially oxidizing a sulfide, or substantially reducing sulfide content, in a fluid such as brines, oil, gas, or combinations of any two or more thereof. Another object of this invention is to provide a process for substantially oxidizing a sulfide, or substantially reducing sulfide content, in a fluid such as brines, oil, gas, or combinations of any two or more thereof. Other objects, and features will become more apparent as the invention is more fully disclosed hereinbelow.

According to a first embodiment of this invention, a bacterial culture is provided which is capable of substantially oxidizing sulfide, or substantially reducing sulfide content, in a fluid.

According to a second embodiment of this invention, a process is provided for substantially oxidizing a sulfide, or substantially reducing sulfide content, in a fluid which comprises contacting the fluid with a composition comprising a bacterial culture which is capable of oxidizing sulfide in a fluid.

DETAILED DESCRIPTION OF THE INVENTION

Figure 1:
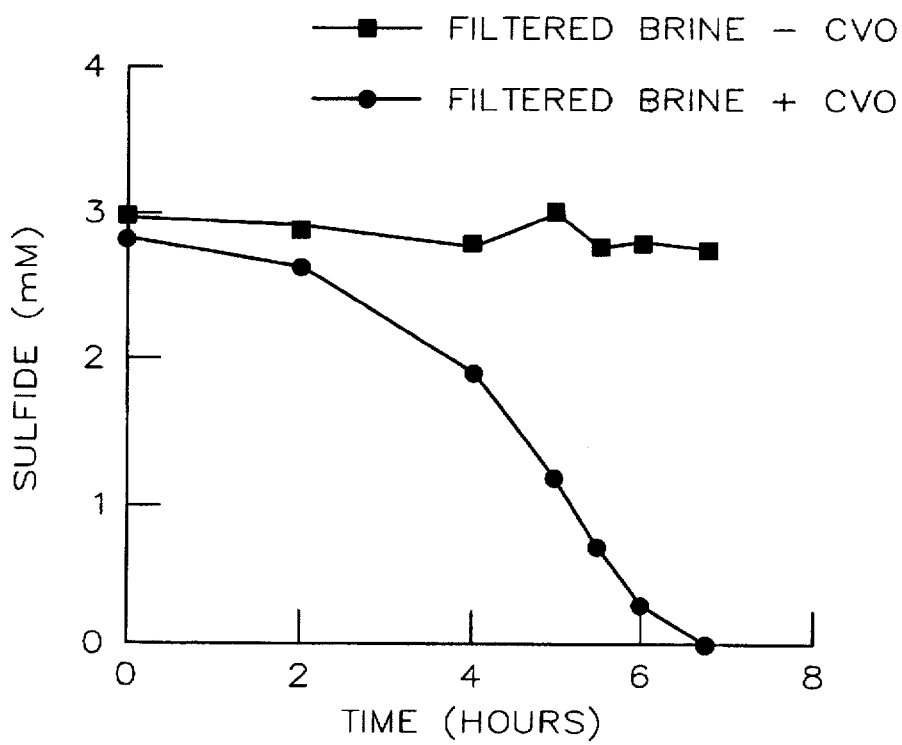
FIG. 1 illustrates sulfide oxidation by Campylobacter sp. CVO (NRRL B-21472) in a filtered brine containing exogenously added potassium nitrate and sodium phosphate (monobasic).

The term "sulfide" used herein in this invention is generically referred to as, unless otherwise indicated, inorganic sulfides, organic sulfides, or combinations of any two or more thereof containing a repeat unit of —$S_n$— in the sulfide molecule wherein n is a number from 1 to about 10, preferably 1 to about 5, and most preferably 1 to 3. The sulfide compounds can be soluble, insoluble, substantially soluble, or substantially insoluble in aqueous media, a non-aqueous media, or combinations thereof. Soluble sulfides, as described above, can be $H_2S$, $HS^-$, $S^{2-}$, or combinations of any two or more thereof.

Examples of sulfide compounds which can be substantially oxidized or removed include, but are not limited to, hydrogen sulfide, dimethyl sulfide, dimethyl disulfide, diethyl sulfide, diethyl disulfide, sodium sulfide, sodium hydrosulfide, potassium hydrosulfide, potassium sulfide, iron sulfide, and combinations of any two or more thereof.

According to this invention, the term "fluid" denotes a liquid, a gas, or combinations thereof. Examples of fluids suitable for use in this invention include, but are not limited to, brines, oil, gas, or combinations of any two or more thereof. The term "brine" or "brines" used in this invention is referred to as, unless otherwise indicated, water, a solution, a suspension, or combinations of any two or more thereof. Generally a solution contains soluble substance such as salts. The suspension can also contain dissolved, partially dissolved, or undissolved substances such as salts. Examples of salts include, but are not limited to, metal salts, such as, for example, sodium chloride, potassium chloride, calcium chloride, calcium bromide, magnesium chloride, magnesium bromide, sodium bicarbonate, sodium sulfate, ammonium chloride, sodium sulfide, sodium hydrosulfide, potassium hydrosulfide, potassium sulfide, iron sulfide, and combinations of any two or more thereof. Generally, total salts content in a solution or suspension can vary widely from, for instance, about 0.5 to as high as about 50 weight percent (%). The presently preferred brine is a produced brine which sometimes is also referred to as oil field brine, or produced water, or petroleum brine, or reservoir brine and is a brine coproduced with oil, or gas, or both. A produced brine generally is contaminated with some oil, or gas, or both.

According to the first embodiment of this invention, a bacterial culture comprising, or consisting essentially of, or consisting of, a sulfide-oxidizing bacterium is provided which is capable of oxidizing sulfide compound in a sulfide-containing fluid. The oxidation product of sulfide or portions thereof in this invention generally comprises elemental sulfur. The term "portions" is used herein to denote any fractions of sulfide. The bacterium is a Campylobacter-like species.

Bacteria known to oxidize a sulfide compound generally produce a sulfate compound. Such bacteria, for example, Thiobacilli, generally do not oxidize a sulfide compound to elemental sulfur. The bacteria disclosed in this application, however, oxidize a sulfide compound or portions thereof to elemental sulfur, especially in mixed cultures, thereby eliminating the problem of producing sulfate which is in turn reduced by SRB to a sulfide compound. Oxidizing a sulfide to elemental sulfur is indeed surprising.

These novel bacteria were isolated by enrichment of a produced brine obtained from brines collected from free-water knockout tank at the Coleville Unit, Coleville, Saskatchewan, Canada. The enrichment yielded two strains of bacteria which have been given laboratory designations of CVO and FWKO B, and assigned accession numbers of NRRL B-21472 and NRRL B-21473, respectively.

The designations of NRRL B-21472 and NRRL B-21473 reflect the fact that the bacterial cultures CVO and FWKO B have been deposited on Jun. 20, 1995 with an official depository, the United States Department of Agriculture, Agricultural Research Service, Northern Regional Research Laboratory, Peoria, Ill. 61604, U.S.A. The deposits have been made under the Budapest Treaty and according to the United States Patent and Trademark Office practice such that all restrictions on availability of the strains to the public will be irrevocably removed upon granting of a patent on this application, of which these important novel strains are the subject. Thus the strains will be available to the public for utilization according to this invention.

Set forth in Table I below are the concentrations of various elements used in enriched medium for growing the novel strains of Campylobacter sp. strains NRRL B-21472 and NRRL B-21473. The concentration in each instance is expressed as of the element, though it is recognized that all or part of each can be present in the form of a soluble ion, such as where P is present in a combined form such as, for example, phosphate.

TABLE I

| | Weight of Element per Liter of Medium | | |
|---|---|---|---|
| Element, Units | Broad Range | Preferred Range | Most Preferred |
| P, g | 0.0001–3.0 | 0.001–2.0 | 0.001–1.0 |
| K, g | 0.01–5.0 | 0.05–4.0 | 0.1–2.0 |
| Mg, g | 0.001–4.0 | 0.005–2.0 | 0.01–1.0 |
| Ca, g | 0.001–4.0 | 0.005–2.0 | 0.01–1.0 |
| S, g | 0.001–5.0 | 0.01–3.0 | 0.05–1.5 |
| Fe, mg | 0.001–5.0 | 0.01–3.0 | 0.05–1.5 |
| Zn, mg | 0.0001–3.0 | 0.0005–2.0 | 0.001–1.0 |
| Mn, Mg | 0.0001–3.0 | 0.0005–2.0 | 0.001–1.0 |
| Cu, mg | 0.00001–1.0 | 0.00005–0.5 | 0.0001–0.5 |
| Mo, mg | 0.00001–1.0 | 0.00005–0.5 | 0.0001–0.5 |
| Co, mg | 0.00001–1.0 | 0.00005–0.5 | 0.000.1–0.5 |
| B, mg | 0.00001–1.0 | 0.00005–0.5 | 0.0001–0.5 |

Sulfur desirably is employed in the form of sulfate. Some of the metals required are advantageously added in the form of a sulfate. Thus, the minimum concentrations of sulfur normally are exceeded. Preferably, magnesium, calcium, iron, zinc, copper, manganese and cobalt are employed in the form of a sulfate, or in the form of a compound which is converted in-situ to a sulfate. Preferably, molybdenum and boron are employed in a soluble form such as, for example, the molybdate and borate, respectively. Potassium preferably is employed as a sulfate or phosphate, or in the form of a compound which is converted in-situ to a sulfate or phosphate. The phosphorus preferably is employed in the form of phosphoric acid or in the form of a phosphate (monobasic), or phosphate (dibasic), e.g., as a potassium or ammonium salt, or as a compound which is converted in-situ to such a salt. While nitrogen is also required for the production of cell mass, no minimum required levels are set forth above because such minimum values can be readily available depending on desired cell mass and because a nitrogen-containing compound is used as a means to grow cell mass.

Generally, any inorganic or organic nitrogen-containing compounds can be used as a nitrogen source. The presently preferred nitrogen source is an inorganic nitrogen-containing compound such as, for example, ammonium salts, metal nitrate salts, or combinations of any two or more thereof. Examples of suitable nitrogen sources include, but are not limited to, ammonia, ammonium nitrate, ammonium chloride, ammonium sulfate, sodium nitrate, potassium nitrate, magnesium nitrate, and combinations of any two or more thereof. Any organic compounds which are generally employed to support the growth of microorganisms can be used as carbon, or energy, or both, source. The presently preferred carbon or energy source is an acetate. Other elements such as, sodium, selenium, iodine, can also be present in the growth medium.

The bacteria of this invention can be grown in any suitable vessels in the absence of oxygen. The growth temperature can vary somewhat, but generally in the range of from about 10° C. to about 40° C., preferably about 10° C. to about 35° C., and most preferably 20° C. to 35° C. The bacteria can grow under a variety of pressure in the range of from about 0.5 to about 15 atmospheres (atm), preferably about 0.5 to about 10 atm, and most preferably 0.9 to 5 atm. The pH of the growth medium can vary from about 5 to about 8.5, preferably about 6 to about 8.5, and most preferably 7 to 8.

The process of this invention can also be carried out continuously. For example, the contacting of a fluid with the bacterial culture can be done by employing continuous stir tank reactors, reactors connected in series, plug flow reactors, packed columns or towers, or other continuous flows that are readily within the realm of one skilled in the art.

Strain CVO is a Gram-negative rod, 0.4 µm in diameter and 0.5–2.0 µm in length, nonmotile under standard culture conditions, and nonsporeforming. It grows anaerobically, with no growth observed under microaerophilic conditions. Strain FWKO B is a Gram-negative rod, 0.4 µm in diameter and 2.0–4.0 µm in length, motile and nonsporeforming. This strain is probably microaerophilic (due to growth in gradient media with sulfide and oxygen) and grows anaerobically as well. These two strains CVO (NRRL B-21472) and FWKO B (NRRL B-21473) have been further characterized as follows in Table II.

in the GenBank database indicated that strain CVO most closely resembled a Campylobacter-like organism. Based on this information, a 16S rRNA-targeted oligonucleotide probe was constructed to a unique region present in the 16S rRNA sequence of strain CVO. Oligonucleotide probes ranged in length from 16 to 21 bases.

Tests for specificity of 16S rRNA-targeted probes were conducted using whole cells. Cells were spotted onto a nylon membrane at a concentration of $5 \times 10^7$/slot and lysed by baking according to the method of Braun-Howland et al (Braun-Howland, E. B., Vescio, P. A., and Nierzwicki-Bauer, S. A., 1993, Use of a Simplified Cell Blot Technique and 16S rRNA-Directed Probes for Identification of Common Environmental Isolates, Appl. Environ. Microbiol., 59:3219–3224). Blots were prewashed twice with 1X SET buffer (0.15M NaCl, 1 mM EDTA, 0.02M Tris; final pH to 7.8) containing 0.1% SDS, hybridized overnight with radiolabeled oligonucleotide probe, washed several times with SET buffer containing 0.1% SDS, and visualized by autoradiography. Cells from closely related genera (*Thiobacillus denitrificans*, *Thiomicrospira denitrificans*, *Sulfurospirillum deleyianum*, *Arcobacter nitrofigilis*, Campylobacter sp. DSM806), as well as other brine isolates were used as negative controls. In addition, blots were probed with a general eubacterial probe (EUB) as a positive control (see Braun-Howland et al; above).

One of the probes tested reacted specifically with strain CVO and cells obtained from an enrichment of production

TABLE II

Media[a] Tested for Growth of CVO and FWKO B

| Media | Substrate | Growth Standard | Growth[b] CVO | FWKO B |
|---|---|---|---|---|
| 295[c] | Thiosulfate + KNO$_3$ | *Thiobacillus denitrificans* | – | – |
| 295 (agar plates) | Thiosulfate + KNO$_3$ | *Thiobacillus denitrificans* | + (slow) | not determined |
| 1255[d] | Thiosulfate + KNO$_3$ | *Thiomicrospira denitrificans* | – | – |
| Campylobacter medium[e] | Aspartate | Campylobacter sp. DSM 806 | – | – |
| Brucella agar[f] | | *Arcobacter nitrofigilis* | – | – |
| Modified Gradient Media (Beggiotoa)[g] | Sulfide + O$_2$ | | – | + |
| Sulfurospirillum medium[h] | fumarate | *Sulfurospirullum delayianum* | – | – |

[a]Media used, unless indicated in the Table, were liquid media.
[b]+ indicates growth, visually, at least 2 days after inoculation (initial cell density about $10^7$ cells/ml).
– indicates no increase in turbidity, at least 2 days after inoculation (initial cell density about $10^7$ cells/ml).
[c]See ATCC catalog (S-8 medium for Thiobacilli).
[d]See ATCC (American Type Culture Collection) catalog (*Thiomicrospira denitrificans* medium).
[e]See DSM (Deutsche Sammlung von Mikoorganismen und Zellkulturen GmbH, Germany) catalog (medium 121).
[f]See DIFCO manual, DIFCO Laboratories, Detroit, Michigan.
[g]Modified gradient medium (agar) was prepared with 0.5% NaCl and is modified from Nelson, D.C., 1992, The genus Beggiotoa. In: The Procaryotes. A Handbook on the Biology of Bacteria. Ecophysiology, Isolation, Identification, Applications, Second Ed. Vol. III. A. Balows, H. G. Truper, M. Dworkin, W. Harder and K. -H. Scheifer, editors. Springer-Verlag, New York. 2638–2657.
[h]See DSM catalog (medium 541).

Strain CVO was further identified by sequencing of the 16S rRNA gene from CVO cells following PCR amplification of purified chromosomal DNA. A 550 base pair fragment of DNA from strain CVO corresponding to regions 350–900 of the *E. coli* 16S rRNA gene was amplified, cloned and sequenced. Comparison of this sequence with sequences in the GenBank database indicated that strain CVO most brine (designated 59-20). The specificity of the probe was demonstrated by lack of hybridization to other similar species and isolates. Hybridization of the probe to cells from the production brine indicated the presence of similar bacteria in this sample. The general eubacterial probe, EUB, reacted with all of the samples, as expected.

A second Campylobacter-like species, designated FWKO B (NRRL B-21473), that was similar to but distinct from strain CVO, as determined by chromosomal hybridization studies was also isolated and purified.

On the basis of the information discussed and demonstrated above, both strains CVO and FWKO B are believed to be strains of Campylobacter species, and are referred to as Campylobacter-like species in this application.

According to the second embodiment of this invention, a process which can be used in applications such as oxidizing a sulfide in a fluid such as brines, oil, or gas is provided. The process comprises, or consists essentially of, or consists of, contacting a fluid with a bacterial culture comprising, or consisting essentially of, or consisting of, a bacterium which is capable of oxidizing sulfide, which is a Campylobacter species. The scope and other descriptions of the bacterial culture and fluid are the same as those disclosed in the first embodiment of the invention.

The contacting of the fluid with the bacterial culture can be carried out by any means known to one skilled in the art. For example, the bacterial culture containing the necessary growth elements can be added to a fluid for a sufficient period of time to substantially reduce a sulfide compound. Thereafter, the bacterial culture, or spent growth medium, or both, can be separated from the fluid. The fluid having reduced sulfide content can then be used in a variety of applications. Because the growth of a bacterium and the separation of a fluid from bacterial cell mass and spent growth medium are well known to one skilled in the art, description of which is omitted herein for the interest of brevity.

For some applications such as, for example, enhanced oil recovery involving the injection of a fluid such as brine into a subterranean formation, the bacterial culture and spent medium do not have to be separated from the fluid. The bacterial culture in a brine can be injected into a formation. The nature of the formation is generally not important and the injection can be carried out by any means known to one skilled in the art such as, for example, pumping.

Alternatively, a fluid such as sulfide-containing gas can be added to a bacterial culture containing the growth medium. The addition of gas fluid to an aqueous medium can be carried out by any means known to one skilled in the art such as, for example, bubbling the gas fluid into or through the aqueous medium.

The time required for the contacting of a fluid with a bacterial culture disclosed in the second embodiment of this invention can be any length of time so long as it is sufficient to effect the oxidation of a sulfide in the fluid. The time required can also be dependent on the concentrations of both sulfide and bacterial cells in the fluid and can be as short as about 30 minutes to as long as about one week. For example, if the concentration of inoculum is $10^7$ cells/ml and the sulfide concentration in the fluid is about 5 mM, it can take about 2 to about 20 hours to substantially oxidize the sulfide.

The following examples are provided to illustrate the present invention and are not intended to unduly limit the scope of the present invention. The growth temperature, unless otherwise indicated, was 30° C.

EXAMPLE I

This example demonstrates biologically-mediated sulfide oxidation using enrichment cultures of brine collected at the Coleville Unit, Saskatchewan.

Oil reservoir brine of low salinity (0.71% total dissolved solids) was collected, in sterile bottles under strictly anaerobic conditions, from a sandstone formation in Saskatchewan by Phillips Petroleum Co. The brine was collected from an oil/water separator tank at a point which was prior to reinjection into the reservoir (hereafter referred to as injection brine). Preparation of all media and cultures including incubations were performed under anaerobic conditions. The major ions present in the brine were sodium (0.29%), chloride (0.41%), bicarbonate (0.19%), sulfate (0.026%), and ammonia (0.001%), and the pH was 7.5. This brine contained 3.3 mM soluble sulfide, which was assumed to have been generated biologically due to the moderate reservoir temperature (30°–35° C.). Sulfide was determined colorimetrically using a methylene blue method. See also Fogo, L. K. and Popowski, M.; Spectrophotometric Determination of Hydrogen Sulfide, Anal. Biochem. 21:732–734 (1949). Because the method is well known to one skilled in the art, description of which is omitted herein.

The total number of bacteria present was estimated at $0.5-1.0 \times 10^7$ cells/ml by direct count using acridine orange. Fermentative, denitrifying, sulfate-reducing, and sporeforming bacteria were all present in the brine, as demonstrated by growth in enrichment cultures and on agar plates. SRB represented approximately 1% of the microbial population at this site, or $10^4-10^5$/ml, using a lactate medium formulated by American Petroleum Institute (API). The assays were set up in triplicate, as used in most probable number (MPN) assay. However, for simplicity, estimates of numbers were made from raw data, rather than performing an MPN calculation.

It was found that sulfide oxidation took place readily when nitrate and phosphate were added to brine enrichment cultures. For instance, after the addition of 5 mM $KNO_3$ and 100 µM $KH_2PO_4$, the sulfide level was reduced from 3.3 mM to a nondetectable level (<0.1 mM) in 48 hours at 30° C. In contrast, there was no change in the control medium which did not contain the nitrate. With added phosphate and nitrate, there was a 10-fold increase in cell number by direct count when compared to controls, indicating that growth was taking place. Similar rates for sulfide oxidation using brines from three production wells were also observed implying that sulfide-oxidizing bacteria are distributed throughout the formation.

It was also found that increasing levels of nitrate stimulated sulfide oxidation, up to 2.5 mM, at which point the sulfide level was reduced to nondetectable. These results demonstrate that sulfide oxidation was nitrate-dependent.

Analyses of spent enrichment cultures, described above, for sulfate, sulfite, and total soluble sulfur indicated that a soluble sulfur oxidation product such as sulfate did not accumulate. During the oxidation process, however, a yellowish-white precipitate appeared in the enrichment bottles. Analysis of this insoluble material by X-ray diffraction and electron dispersion spectroscopy indicated that it was a mixture of elemental sulfur and calcite. Nitrate reduction resulted in the formation of nitrite and nitrogen gas. There was no net increase in ammonia.

EXAMPLE II

This example illustrates the enumeration and identification of sulfide-oxidizing bacteria. This example also demonstrates the oxidation of sulfide in brines and synthetic media using the bacteria of this invention.

Nitrate-reducing, sulfide-oxidizing bacteria were enumerated by MPN, as described in Example I, using oxidation of the redox indicator resazurin as a growth indicator. Using indicator resazurin is a method well known to one skilled in the art. Approximately $10^4$ sulfide-oxidizing bacteria/ml were present in samples of injection brine, and samples from three producing wells. Plating of enrichment cultures from injection brine on 295 agar medium (see footnote a, Table II) resulted in the purification of several colony types of bacteria. One of the isolates obtained, CVO (NRRL B-21472), was a Gram-negative rod capable of oxidizing sulfide when inoculated into filter-sterilized brine supplemented with nitrate and phosphate (see FIG. 1). Filter-sterilized brine was Coleville brine collected at the free-water-knockout and filtered through a 0.2 μm cellulose-acetate filter to remove bacterial cells. Inoculation was done with 2 ml of a culture that contained about $10^7$ cells per ml.

Figure 2:
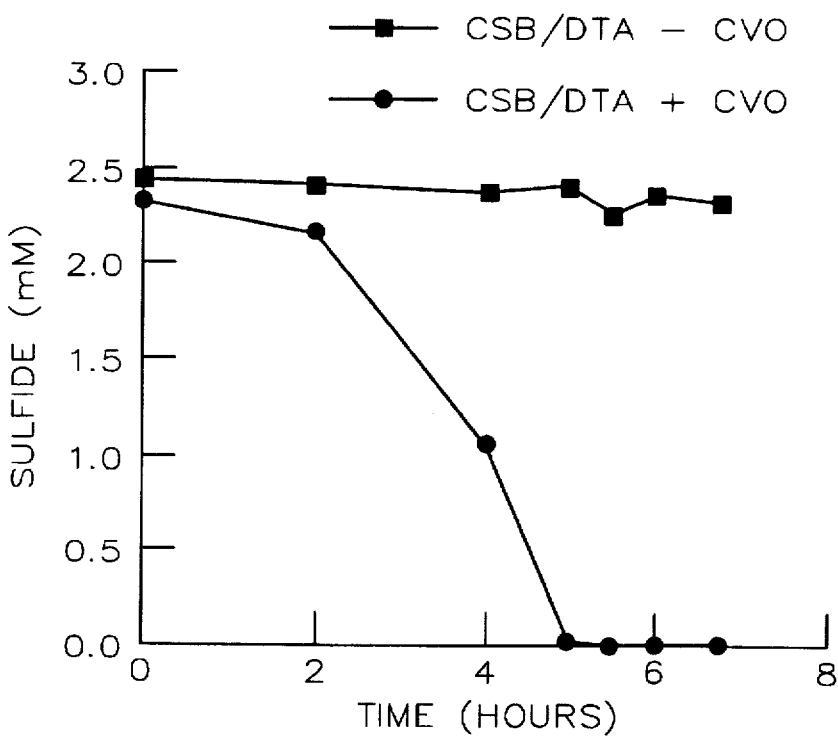
FIG. 2 shows sulfide oxidation by Campylobacter sp. CVO (NRRL B-21472) in CSB/DTA medium.

FIG. 1 shows the oxidation of sulfide by strain CVO in filtered brine supplemented with 5 mM $KNO_3$ and 100 μM of sodium phosphate ($NaH_2PO_4$). Without the presence of CVO cells (−CVO, FIG. 1), there was little or no sulfide oxidation. In the presence of cells of strain CVO (+CVO, FIG. 1), however, sulfide oxidation rapidly occurred. Similar results were obtained when synthetic medium CSB/DTA was used in place of filtered brine (FIG. 2). The medium composition of CSB/DTA is shown in Table III. The results shown in FIG. 1 and FIG. 2 demonstrate that the bacteria of this invention catalyzed the oxidation of sulfide in either oil field brines or in synthetic media.

TABLE III

CSB/DTA Medium

| CSB base (in g/l) | |
|---|---|
| NaCl | 7.0 |
| $MgSO_4 \cdot 7H_2O$ | 0.68 |
| $CaCl_2 \cdot 2H_2O$ | 0.24 |
| $NH_4Cl$ | 0.02 |
| $NaHCO_3$ | 1.90 |
| Add DTA solution: | |
| ND Stock Solution | 50 ml |
| $(NH_4)_2SO_4$ | 0.13 |
| $KNO_3$ | 1.0 |
| $KH_2PO_4$ | 0.027 |
| Sodium Acetate | 0.68 |
| Resazurin (0.1%) | 1 ml |
| 1M $NaS \cdot 9H_2O$ stork | 5 ml/l |
| Adjust pH to 7.5; aliquot in Coy chamber and sterilize. | |
| ND Stork Solution (in g/l) | |
| Nitriloacetic acid | 2.0 |
| Micronutrient solution | 10 ml |
| $FeCl_3$ solution (0.29 g/l) | 20 ml |
| $CaSO_4 \cdot 2H_2O$ | 1.2 |
| $MgSO_4 \cdot 7H_2O$ | 2.0 |
| NaCl | 0.16 |
| $Na_2HPO_4$ | 1.4 |
| $KH_2PO_4$ | 0.72 |

| Micronutrient solution | |
|---|---|
| Distilled water | 1,000 ml |
| $H_2SO_4$ (concentrated) | 0.5 ml |
| $MnSO_4 \cdot H_2O$ | 2.28 g |
| $ZnSO_4 \cdot 7H_2O$ | 0.50 g |
| $H_3BO_3$ | 0.50 g |
| $CuSO_4 \cdot 5H_2O$ | 0.025 g |
| $Na_2MoO_4 \cdot 2H_2O$ | 0.025 g |
| $CoCl_2 \cdot 6H_2O$ | 0.045 g |

Figure 3:
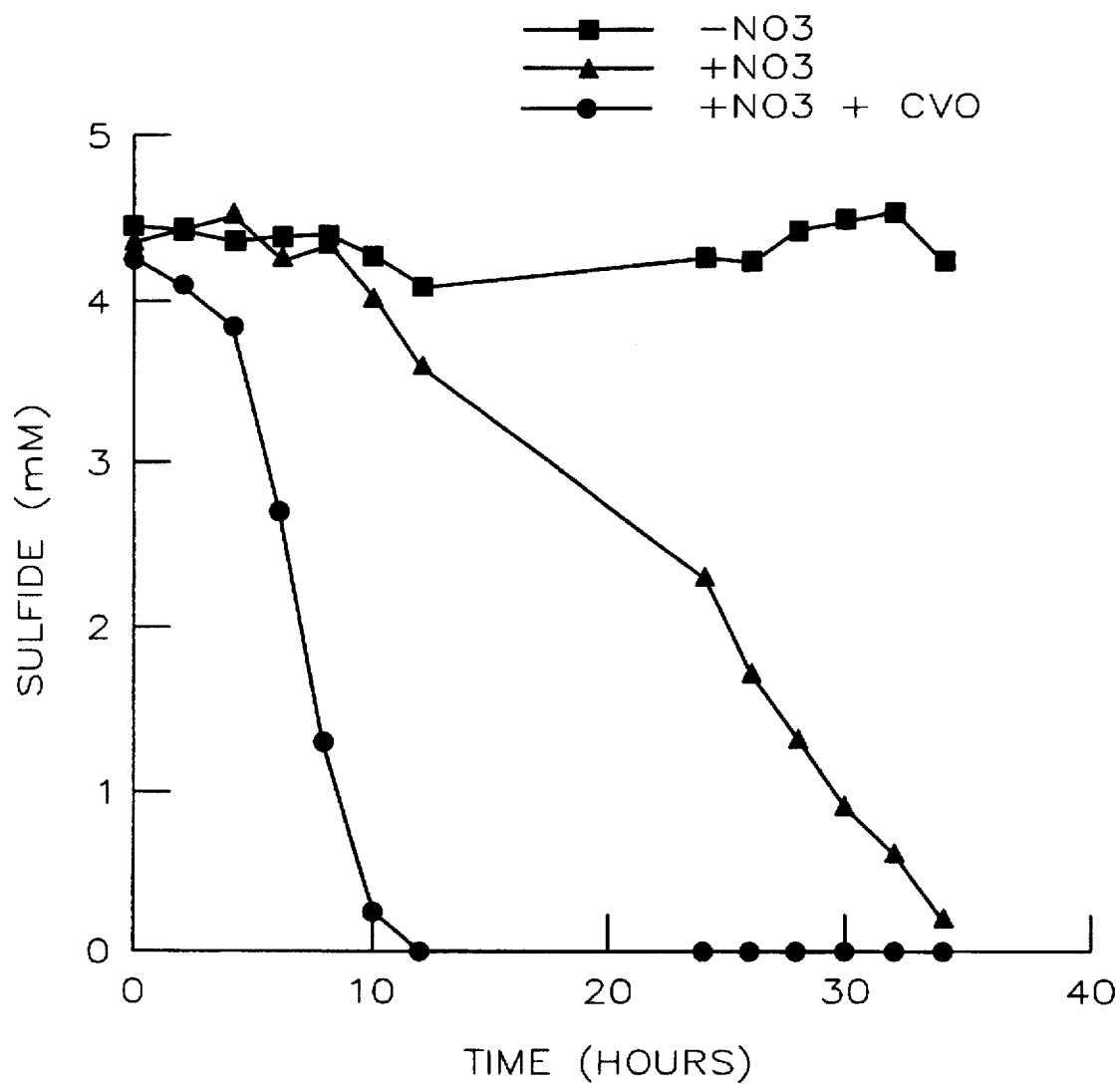
FIG. 3 illustrates the synergistic effect of combining Campylobacter sp. CVO (NRRL B-21472), potassium nitrate, and sodium phosphate (monobasic) in a produced brine on sulfide oxidation.

FIG. 3 illustrates the enhancement of sulfide oxidation by adding CVO cells to natural produced brine. The run was carried out as follows. Enrichments with an unfiltered production brine having the composition as shown in the CSB base (first five lines of Table III), containing 4.4 mM soluble sulfide, were prepared by adding 50 ml of brine, 5 mM $KNO_3$, and 100 μM $NaH_2PO_4$ to serum bottles. In one case, the brine was supplemented with 2 ml (about $10^7$ cells/ml) of a culture of strain CVO that was gown overnight. The addition of the strain CVO lessened the lag time considerably, and reduced the time needed for complete oxidation of the sulfide from more than about 34 hours to less than about 12 hours.

EXAMPLE III

This example illustrates sulfide oxidation rate of Campylobacter-like species of this invention.

The runs were carried out with free-water knockout (FWKO) brine as described in Example II. The brine, set up in triplicate, was filter-sterilized and supplemented with 5 mM $KNO_3$ and 100 μM $NaH_2PO_4$ (stock solution of these were sterilized separately). Each run shown in Table IV below was inoculated with cultures containing about $10^7$ cells/ml as noted in Table IV. Sulfide was measured as described in Example I.

TABLE IV

| | Sulfide Levels (mM) | | | |
|---|---|---|---|---|
| Time (Hours) | Filtered Brine | CVO | FWKO-B | Unfiltered Brine |
| 0 | 2.55 | 2.50 | 2.53 | 3.36 |
| 2 | 2.48 | 2.49 | 2.42 | 3.38 |
| 4 | 2.54 | 2.49 | 2.37 | 3.45 |
| 6 | 2.46 | 2.37 | 1.94 | 3.19 |
| 8 | 2.46 | 2.28 | 0.88 | 2.55 |
| 10 | 2.37 | 1.81 | BD[a] | 1.37 |
| 12 | 2.33 | 1.03 | BD | 0.01 |
| 13 | 2.25 | 0.46 | BD | BD |
| 14 | 2.38 | BD | ND[b] | ND |
| cells/ml[c] | ND | $1.2 \times 10^8 \pm 0.2$ | $1.5 \times 10^8 \pm 0$ | $1.0 \times 10^8 \pm 0.1$ |

[a]BD = Below detection (<0.1 mM).
[b]ND = Not determined.
[c]Cell counts were done at 24 hours.

The results shown in Table IV indicate that the sulfide levels in filtered brine control were essentially not changed in 14 hours. The results also show that the rates and lag time for sulfide oxidation were similar for both strains of CVO and FWKO B and unfiltered brine enrichment (last column, Table VI).

After 24 hours of incubation, cell counts for cultures of these four runs shown in Table IV were determined by direct microscopic counts using acridine orange. The results shown in Table IV above indicate that the final cell numbers, except the filtered brine control, were approximately the same.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the specification and the claims.

That which is claimed:

1. A biologically pure bacterial culture capable of oxidizing a sulfide to elemental sulfur in a fluid wherein said bacterial culture is a Campylobacter species selected from the group consisting of Campbylobacter sp. CVO (NRRL B-21472), Campylobacter sp. FWKO B (NRRL B-21473), and combinations thereof and said fluid is selected from the group consisting of brines, oil, gas, and combinations thereof.

2. A bacterial culture according to claim 1 wherein said Campylobacter species is Campylobacter sp. FWKO B (NRRL B-21473).

3. A bacterial culture according to claim 1 wherein said Campylobacter species is Campylobacter sp. CVO (NRRL B-21472).

4. A biologically pure culture of strain Campylobacter sp. CVO (NRRL B-21472).

5. A biologically pure culture of strain Campylobacter sp. FWKO S (NRRL B-21473).

6. A biologically pure bacterial culture capable of reducing a nitrate and oxidizing a sulfide in a fluid wherein said bacterial culture is a Campylobacter species selected from the group consisting of Campbylobacter sp. CVO (NRRL B-21472), Campylobacter sp. FWKO B (NRRL B-21473), and combinations thereof and said fluid is selected from the group consisting of brines, oil, gas, and combinations thereof.

7. A bacterial culture according to claim 6 wherein said Campylobacter species is Campylobacter sp. FWKO B (NRRL B-21473).

8. A bacterial culture according to claim 6 wherein said Campylobacter species is Campylobacter sp. CVO (NRRL B-21472).

9. A bacterial culture according to claim 1 wherein said brine is a produced brine.

10. A bacterial culture according to claim 2 wherein said brine is a produced brine.

11. A bacterial culture according to claim 3 wherein said brine is a produced brine.

12. A bacterial culture according to claim 6 wherein said brine is a produced brine.

13. A bacterial culture according to claim 7 wherein said brine is a produced brine.

14. A bacterial culture according to claim 8 wherein said brine is a produced brine.

* * * * *